United States Patent
Aspichueta et al.

[11] Patent Number: 6,053,733
[45] Date of Patent: Apr. 25, 2000

[54] DENTAL IMPLANT

[75] Inventors: Santiago Aldama Aspichueta; Beatriz Aldama Bolunburu, both of Vitoria, Spain

[73] Assignee: Beatriz Aldama Bolunburu, Vitoria, Spain

[21] Appl. No.: 09/319,557

[22] PCT Filed: Oct. 8, 1998

[86] PCT No.: PCT/ES98/00277

§ 371 Date: Aug. 5, 1999

§ 102(e) Date: Aug. 5, 1999

[87] PCT Pub. No.: WO99/18881

PCT Pub. Date: Apr. 22, 1999

[30] Foreign Application Priority Data

Sep. 10, 1997 [ES] Spain ................................ P 9702104

[51] Int. Cl.[7] .................................................. A61C 8/00
[52] U.S. Cl. ........................................... 433/173; 433/176
[58] Field of Search .................... 433/172, 173, 433/174, 175, 176, 201.1

[56] References Cited

U.S. PATENT DOCUMENTS

| | | | |
|---|---|---|---|
| 4,842,518 | 6/1989 | Linkow et al. | 433/174 |
| 4,854,872 | 8/1989 | Detsch | 433/173 |
| 5,000,686 | 3/1991 | Lazzara et al. | 433/174 |
| 5,312,256 | 5/1994 | Scortecci | 433/173 X |
| 5,316,476 | 5/1994 | Krauser | 433/173 |

*Primary Examiner*—Nicholas D. Lucchesi
*Attorney, Agent, or Firm*—Browdy and Neimark

[57] ABSTRACT

A dental implant with a straight cylindrically shaped upper end finishing off in a hexagonal projection, with both being axially perforated in alignment with the screw-threaded stem. The perforation does not exceed the lower end of the cylindrical portion and the screw-threaded stem can be made with an appreciably smaller diameter than the conventional one. The apical (apexial) end of the stem is conical and is finished off by a small chamfer or bevel. This favours reaching the cortical area of the bone, increasing the guarantees of its immobility, as well as performing a better crushing and grinding of the bone.

2 Claims, 3 Drawing Sheets

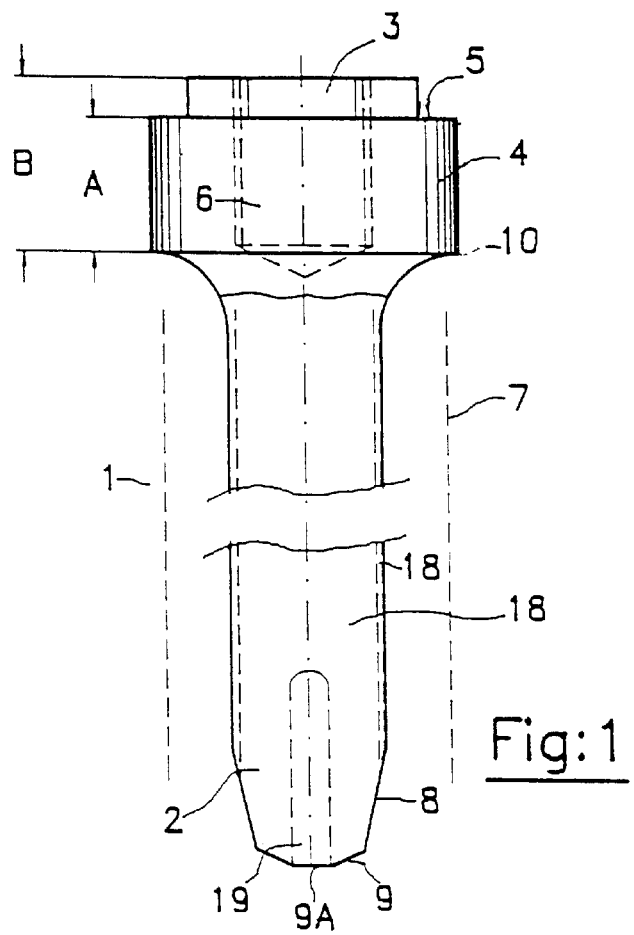
Fig:1
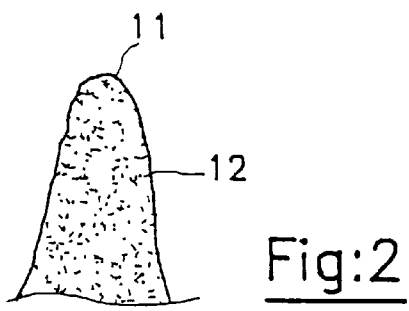
Fig:2
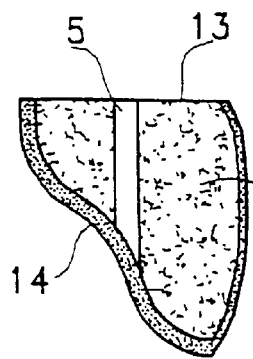
Fig:3
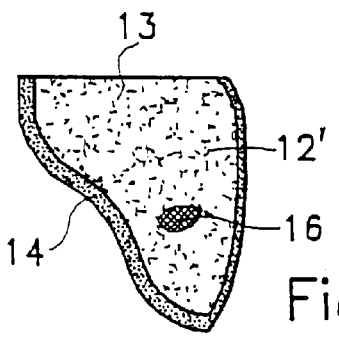
Fig:4

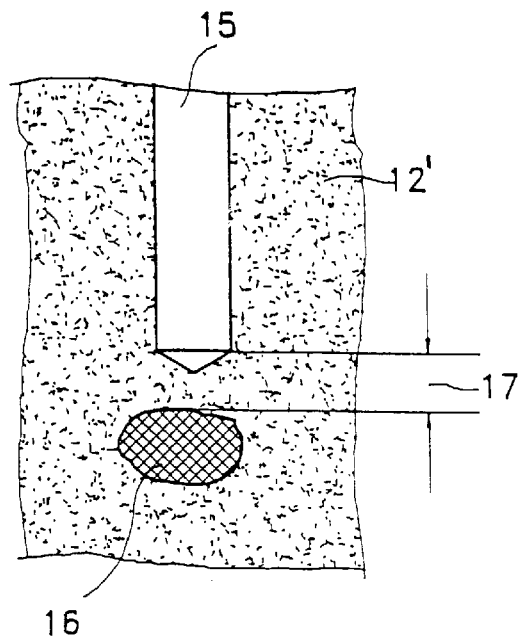
Fig:5
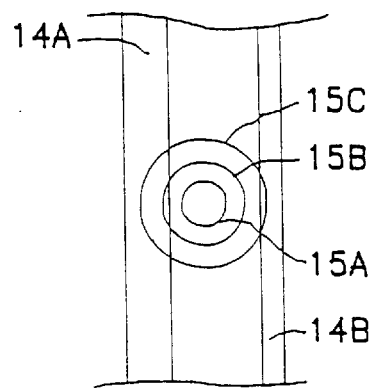
Fig:6
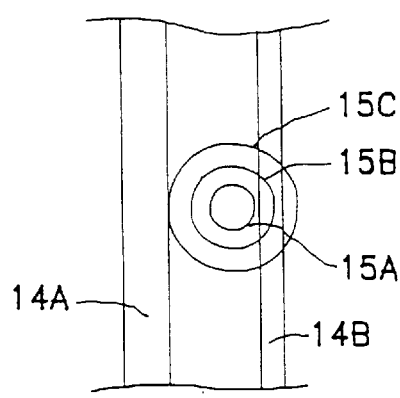
Fig:7
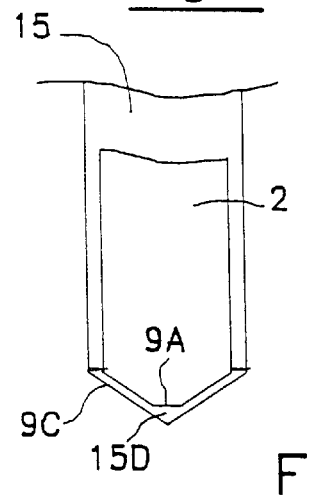
Fig:8
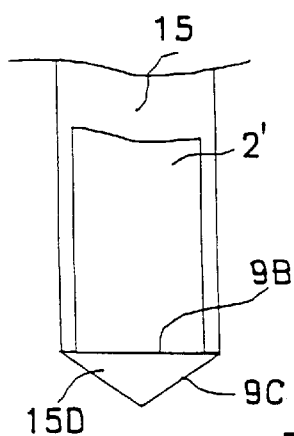
Fig:9

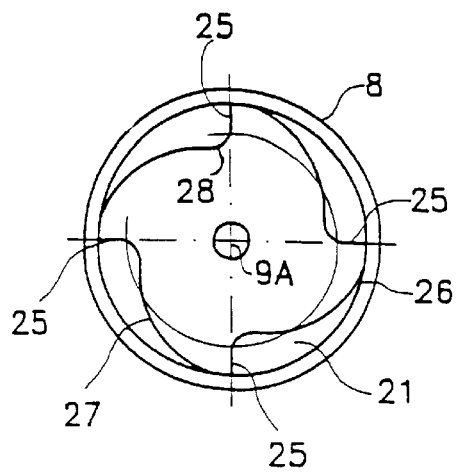
Fig:10
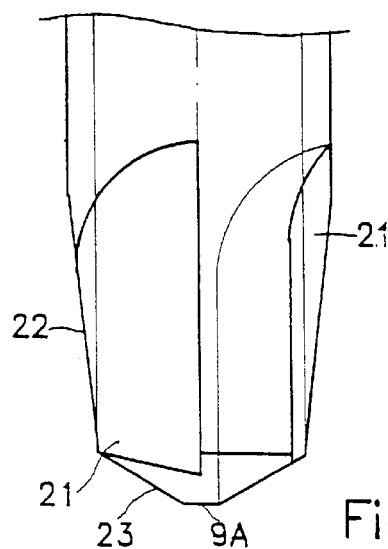
Fig:11
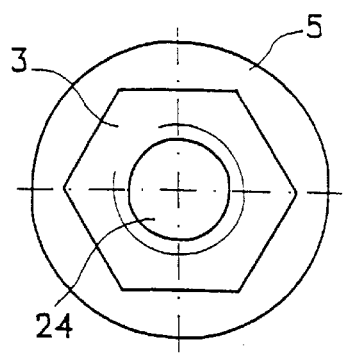
Fig:12
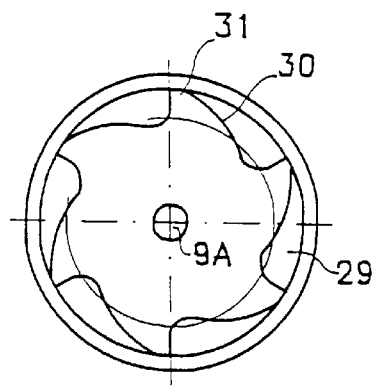
Fig:13
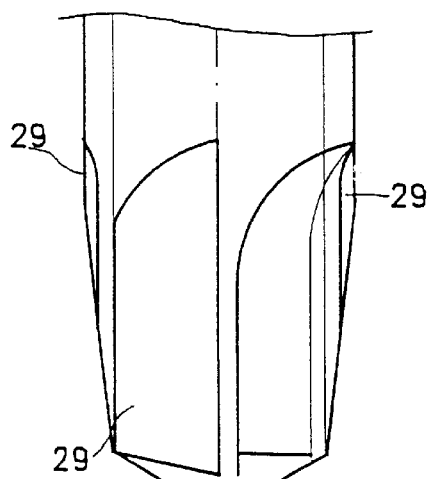
Fig:14
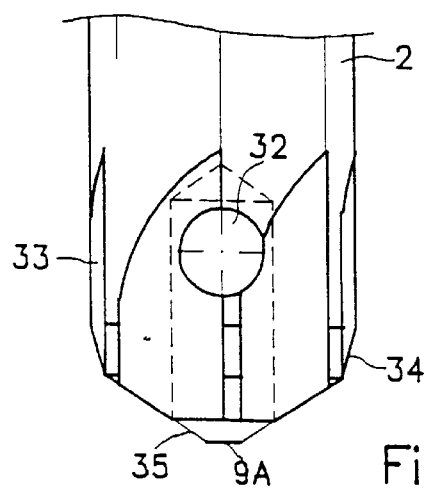
Fig:15

DENTAL IMPLANT

This invention relates to a dental implant of the type used by dental surgeons for insertion into the maxillary bone of the jaws of patients, so that they act as a firm base on which to assemble false teeth or dentures.

The general technique for these implants was suggested more than twenty years ago by the Swedish professor Dr. Brånemark and a great many variations on this are known, aimed at improving or trying to improve their characteristics in order to increase their effectiveness.

In general terms, a dental implant is a unit that is housed in the jawbone of the patient, by suitably securing it to the bone, until the upper area or coronal is reached. In this area, the implant is provided with means to enable the stable fixing of a false tooth. In order to perforate the bone, it is first milled, at least, so as to obtain a hollow cylindrical internal cavity with a flat surface, which is later screw threaded with another tool, for example a tap, in order to obtain a screw-threaded internal cavity in which the implant can be suitably secured.

This latter screw threading operation of the flat-sided perforation in the bone is usually carried out by means of the implants themselves, called self-tapping, already known for many years and which base their technique on the already mentioned system of the taps.

Through patent U.S. Pat. No. 2,388,482, a surgical instrument to make perforations in the bones of patients is known, which is provided with a screw-threaded area, finishing off in a portion equipped with four longitudinal recesses, which in turn is finished off by its characteristic apical end.

Moreover, the existence is also known, through publication U.S. Pat. No. 2,472,103, of a tool to carry out the screw threading, which has a cylindrical portion provided with a helicoidal screw thread which is finished off by another conical end portion, in which the said screw thread continues to extend itself, with this latter conical area being provided with longitudinal slots or grooves that favour the insertion of the tool.

Also known, by means of U.S. Pat. No. 2,609,604, is a conical implant provided with a helicoidal screw thread with a multitude of longitudinal slots that extend radially along its outer periphery.

Through U.S. Pat. No. 3,435,526, an implant is known that has a polygonal head, e.g. with a hexagonal cross section, so that it can be used during fixing to the bone, followed by another flat cylindrical portion, which gives way to another cylindrical portion with a smaller diameter, which is screw threaded and has holes passing through it. The end of this implant is trunco-conical and longitudinal slots circulate from this end.

An implant is also known through U.S. Pat. No. 3,672,058 whose body is conical and is occupied by a helicoidal screw thread of a large pitch, which is also provided with longitudinal slots. This implant is self-tapping and its internal or apical end is conical with an angle of approximately 10 degrees in order to facilitate its insertion.

The tap teeth or threads have, starting from its conical apical head, a progressive increase both in the head radius and in the base radius, given that the base of the body is totally conical.

Through the patent FR.A. 2,395,738, a conical implant is also known which is provided with helicoidal teeth and slots, both straight longitudinal ones and inclined or slanting ones.

In U.S. Pat. No. 4,324,550 an implant is described, also conical, provided with tap teeth or threads, in which there are also longitudinal slots, which in turn have cutting edges that facilitate the screwing of the implant into the bone.

Also known through the German publication "Rund um die werkzeugmaschine", published in Spain under copyright in 1957, Editorial Reverté, S. A., are taps with their cylindrical body finished off at the end by a trunco-conical portion, with both being provided with helicoidal teeth or threads and with longitudinal slots that provide cutting edges.

U.S. Pat. No. 4,406,623 presents an implant which is conical and is provided with helicoidal teeth that extend along the whole of its body, until the apical end, which can finish in a cone of approximately 90 degrees. A set of slots in a helicoidal direction interrupt the teeth and provide cutting edges that facilitate the insertion of the implant, which is self-tapping.

Some of these implants mentioned have, at their head, a blind hole perforated in an axial direction into which a screw is threaded that later incorporates the false tooth. This hole extends, starting from the polygonal end, going through the level of the adjoining flat cylindrical portion until it traverses a considerable length of the screw-threaded area of the implant, so that it obliges the diameter of this screw-threaded area to be considerable so as to keep it suitably strong.

This means a considerable inconvenience or disadvantage in many cases, given that it makes it enormously difficult to situate the implant in narrow bone ridges in patients, due precisely to the diameter of the portion provided with the screw thread.

On the other hand, it is extremely well known in odontology techniques that an implant obtains a better fixing in the bone of the patient when it reaches the cortical bone, so there is a tendency to favour implants being screwed into the said cortical bone, which is considerably harder than the portion of the medular bone.

Moreover, there is the problem of the dental nerve in the rear area of the jaw, which it is important not to impinge upon with the implant inn order to avoid the very serious disadvantages that this causes.

In this respect, operations to insert an implant normally begin, as mentioned previously, with the milling of the bone in order to provide a flat-sided cylindrical cavity prior to the insertion of the self-tapping implant, which acts as a tap.

In the drilling operations, specialists drill until they reach the smallest possible distance from the dental nerve. In these operations, the millers are housed at a high number of revolutions, so that once the hole is finished, the treatment with the self-tapping implant begins, working at a very low radial speed.

This habitual practice is not advisable, given that there would be fewer risks by inverting the treatment, i.e. milling the hole to a greater distance from the dental nerve, as with the higher working speed there is less control and inaccuracy in the treatment.

Therefore, the final operation with the self-tapping implant at low radial speed would allow its penetration to be perfectly controlled until it is close to the dental nerve, all with a lower risk for the patient.

On the other hand, all these implants have the general characteristic that on carrying out the internal screw threading of the previously milled hole, some cuts are produced in the shell or films in the bone, bladed cuts that do not in any way favour the later formation of bone mass that binds the implant.

The objective of the invention is to provide a dental implant that enables the diameter of its self-tapping portion to be reduced in the hole in the patient in order to facilitate its insertion in its upper edge when there are extremely narrow ridges.

Another object of the invention is a dental implant that allows it to be bicorticalized, thus achieving a better fixing in the cortical bone.

Another object of the invention is a dental implant that facilitates both the insertion and the formation of the screw thread in the bone of the patient and makes it possible to approach the proximity of the dental nerve with less risk by inverting the way of working the perforation.

Another object of the invention is a dental implant that relieves the friction caused during the screw threading while at the same time it favours the crushing and grinding of the bone for better integration of the implant.

Another object of the invention is a dental implant that allows a more centred placing of the implant in the previously milled hole.

For the implementation of these objectives, the implant of the invention starts with a unit that is provided with the following items, already known by the science:

A generally cylindrical head whose outer face is occupied by a hexagonal projection, for instance included in a theoretical outer diameter that is smaller than the diameter of the transversal cross section of the said cylindrical head.

A blind axial hole starting from the end of the said outer face in order to later receive a support screw for the false tooth.

A cylindrical stem provided with helicoidal teeth or thread, finishing in a trunco-conical end on which the toothing or threading is prolonged along the whole of the side surface.

Some longitudinal slots or grooves, variable in number, that extend from the free apical end of the implant, which are provided with at least one cutting edge.

On the basis of these particulars, the implant in accordance with the invention is characterised in that the straight cylindrical portion of its head, from which the hexagonal projection starts, has a substantially bigger generatrix in comparison to the dimension of traditional ones, so that the blind front screw-threaded hole that passes axially through the implant does not exceed the end plane of the said cylindrical portion.

Therefore, the screw-threaded stem that starts from the cylindrical portion is whole in its cross section and can be smaller in its diameter. This reduction in the diameter of the stem means in practice that it is easier for the implant to be applied in narrow ridges, all without any loss of or detriment to its strength.

From the studies and experiences carried out, it as been observed that good practical results are achieved with the dental implant when the height or dimension of the straight generatrix of the cylindrical portion is situated between 0.7 and 5 millimetres, the total height of the blind screw-threaded hole between 3 and 5 millimetres and the diameter of the stem between 2.5 and 6 millimetres.

By acting between these values and combining them appropriately, the implant is perfectly prepared to face any type of ridge in the bone of the patient, without suffering any type of variation in its correct direction and alignment and without impairing its strength, exactly as described previously.

The neck therefore is wider and allows the housing of the screw that is to hold the prosthesis without weakening the said neck of the implant in the area of its taper, preventing it from breaking. Therefore, the use of implants of a smaller diameter than conventional ones is also facilitated.

In the same way, the hexagonal projection is characterised in that it has a size of between 0.65 and 1 millimetre.

In the same way, the implant in accordance with the invention also claims an apical end with a general cone shape, according to which the angle of this end is 120 degrees. This formation finishes off the screw-threaded end of the trunco-conical stem of the implant provided with incisive longitudinal slots, allowing the milling of the perforation in the bone, which is carried out at a high number of revolutions, to be interrupted at a safety distance from the dental nerve, when working on the tooth in the rear area of the jaw.

In particular, the free end of this apical conical area is flattened off, so that it does not offer sharp edges when it is penetrating. The diameter of this bevelled section is between 15 and 25% of the diameter of the cross section of the implant and is one of the characteristics claimed by the implant.

In the operation of screwing in the implant of the invention, the bevelled taper of the apical end makes it possible to approach the dental nerve without greater risks, given that the speed of rotation during the screwing operation is low and therefore perfectly submitted to a safety control by the specialist.

On the other hand, the conical area of the apical end favours the reaching of the cortical area of the bone, thus allowing the implant to establish itself in this are, which is harder, and increasing the guarantees of its immobility.

In the same way, as the apical end of the implant is incisive, it moves by a lesser amount towards the weaker cortical of the bone.

As is well known as regards the two corticals, in a cut in either of the two maxillaries, the lingual or palatine is generally wider and more ivory-like than the vestibular, and does not become centred as initially foreseen.

For this reason, as the implant is self-centring, with a live tip, it is possible to go deeper into the previously established bed. If necessary, it will be lodged exactly in the space created by the milling tool, as the apical area of the implant has a shape similar to that of the milling tool, not wasting any length of the implant nor leaving any empty holes in the bone.

The trunco-conical area of the self-tapping implant, provided with a screw thread and also longitudinal slots with cutting edges, generally either four or six in number, has a particular cross section, according to which and during the insertion of the implant into the hole, previously milled, for the implant to be screwed in, this is carried out with less friction, while also favouring the better crushing and grinding of the bone for its later integration with the implant itself once it has been inserted.

All this is materialised by means of the specific geometry of the bases of the longitudinal slots arranged between the projections provided on the outer cutting edges of the threads. Therefore, starting from the cutting end situated in a position more distant from the centre of the implant, each cutting edge extends by a certain length according to a radial direction until a point where it makes an outwardly curved concave twist, which is connected in continuity with another outwardly curved convex portion that reaches the cutting end of the adjoining screw threaded projection.

All these and other details of the invention will be appreciated in greater detail and precision by referring to the sheets of drawings which are attached, in which the following are represented, without any kind of limiting nature:

FIG. 1 is an elevation of the implant in accordance with the invention.

FIG. 2 represents a narrow ridge of the bone of a patient.

FIG. 3 is a cross section view of a bone, showing the

FIG. 4 is a cross section of the rear area of the jaw, which shows the dental nerve FIG. 5 is a cross section of a perforation or hole in accordance with the invention, in the area close to the dental nerve.

FIGS. 6 and 7 represent two view which how the different behaviour, normal and displaced, respectively, in relation to the palatine or lingual and vestibular corticals.

FIG. 8 shows the behaviour of the implant in accordance with the invention, in the prior milling carried out in the bone.

FIG. 9 represents the way of operating in a conventional implant.

FIG. 10 shows a bottom view from the apical area of an implant in accordance with the invention.

FIG. 11 is a variant of the apical end of an implant in accordance with the invention.

FIG. 12 is a top view of the implant shown in FIG. 1.

FIG. 13 is a variant of the invention from its apical end.

FIG. 14 is an elevation of an apical end of the implant in accordance with a variant of the invention, which corresponds to FIG. 13.

FIG. 15 is another variant of the apical end of the implant in accordance with the invention.

Looking now at FIG. 1, we can appreciate an implant (1) provided with a screw-threaded portion (2), a head or neck (4) and a hexagonal projection (3) standing out from the upper end (5) of the said neck.

The portion (2) is provided with teeth or screw-threading (18') along the whole of its length, with the exception of its lower or apical end, in which the longitudinal grooves (19) provided with cut-outs, also longitudinal, can be appreciated.

In the same way, the lower end of the implant is shaped by means of trunco-conical tapers (8, 9), in which the portion (9) has an angle of 120 degrees.

This portion (9) is in turn finished off with a chamfer or bevel (9A), which has a circular cross section whose diameter is of the order of between 15 and 25% of the diameter of the screw-threaded portion of the stem or pin of the implant.

The neck or head (4) is of a dimension or size (A) at its generatrix, which, in accordance with the invention, is between 0.7 and 5 millimetres.

The dimension (B), which is the sum of the height of the generatrix of the head (4) and of the height of the projection or, to put it another way, the total depth of the screw-threaded perforation (6), in accordance with the invention, is between 1.4 and 6.5 millimetres.

In turn, the diameter of the screw-threaded portion (18') of the stem or pin (18) of the implant, will be between 2.5 and 6 millimetres, which is substantially less than the conventional diameter, represented by the dotted lines (7).

FIG. 2 shows a habitual narrow ridge (11) of a bone (12), which usually presents difficulties as regards being penetrated by a stein of a large diameter, whereas it can be penetrated perfectly by the stem described by the invention.

With regard to FIG. 3, it shows the preferred characteristic of prior milling (15) or bed of an implant in a tooth (12), carried out from its upper end (13), according to which the cortical bone (14) must be advantageously reached by the implant in order to ensure its better fixing.

In accordance with FIGS. 4 and 5, we can observe a bone (12') corresponding to the rear area of the jaw, with the dental nerve (16) passing through this area. As this nerve must necessarily be avoided, it will be appreciated how the prior milling (15) of the bone (12') can be interrupted a distance (17) from it, within this distance providing the necessary safeguard that the said nerve will not be affected.

After X-ray control, it would be possible to continue with the insertion of the implant at low revolutions, e.g. 15 or 20, until it is as close as possible to the path of the nerve, if necessary.

FIGS. 6 and 7 represent two actions in which the lingual or palatine (14A) and vestibular (14B) corticals of a maxillary are shown. It is frequent that on carrying out the perforation of the bone and due to the greater hardness of the cortical (14A), the different milling operations (15$^a$, 15B, 15C) become displaced towards the vestibular cortical (14B), even reaching the point, on occasions, of breaking this vestibular cortical.

The ideal penetration, shown in FIG. 6, represents how it has been carried out in a centred and correct manner, in which the implant of the invention, with its apical end, also has a minimal tendency to displace itself towards the weaker cortical, providing greater reliability as regards the siting of the said implant.

With reference to FIGS. 8 and 9, we can observe the behaviour of a traditional implant (2'—FIG. 9), which, with its usually blunt or flat end (9B), leaves a space in the bone (15D) (9C, 15D) which is not taken advantage of In accordance with the invention, in FIG. 8, this pace (9C, 15D) is totally occupied by he end of the implant, with its apical end adapting perfectly to the shape of the said bone by its having a similar shape to that of the milling head.

In FIG. 11 we can deduce a practical solution for the apical end of the implant on its stem (2), in which the longitudinal slots or grooves (21) cut in its end can be appreciated. This end is finished off in a conical shape (23) of approximately 120 degrees, with its tip being provided with a chamfered or bevelled surface (9A) that avoids any sharp edges.

The said chamfered surface (9A) has a dimension of between 15 and 25% of the dimension corresponding to the average cross section of the stem (2) of the implant.

FIG. 10 shows the particular geometry of the apical end of the implant with the slots or grooves (21) determined by the longitudinal recesses, in which it is also possible to appreciate the cutting surfaces and ends (25, 26). The geometry of these slots (21) is determined by the outwardly curved concave portions (28), followed by the other outwardly curved convex portions (27), that form the base of the said slots.

The solution proposed by this FIG. 10 represents an end based on four slots, that corresponds technically with the one shown in FIG. 13, which shows the slots (29) and the and the curved concave (31) and curved convex (30) portions, carried out in this solution with six slots.

FIG. 14 represents the side view of the latter and corresponds technically with the one shown in FIG. 11.

In all these, FIGS. 10, 11, 13 and 14, the end chamfer or bevel (9A) that finishes off the apical end of the implant, in accordance with the invention, can be appreciated.

As regards FIG. 12, it represents the hexagonal projection (3) of the implant, standing out from the upper base (5) of the cylindrical portion (4), together with the position (24) that corresponds to the perforation (6) in FIG. 1.

Finally, in FIG. 15, another practical solution for the implant at its apical end can be observed, with longitudinal slots (33) a conical end (34, 35) and a chamfer (9A). In this case, the implant is provided with perforations or holes (32), to be filled in by the bone after it has been implanted.

Moreover, it is pointed out, for the appropriate purposes, and as suggested as being known by U.S. Pat. No. 4,826,434, that that the implant can be treated by surface etching, using techniques which are also known in other fields.

Concentrated acids are usually used for this purpose, as treatment with these considerably increases the roughness of the surface of the implant.

Once that the nature and advantages of this invention have been described, it is important to point out its non-restrictive character, inasmuch as changes in the shape, materials or dimensions of its constituent parts will not in any way alter its essence, as long as they do not mean a substantial variation of the whole assembly.

What is claimed is:

1. Dental implant that has an upper end with a generally cylindrical shape and straight generate, from which a prismatic portion or projection with a hexagonal shape protrudes outward, with this end being perforated axially with a blind internally screw-threaded hole, with an externally screw-threaded stem finished off at its apical end by a trunco-conical portion, also screw-threaded, in turn finished off by another cone shaped end, also provided with longitudinal slots that have cutting edges and procuring screw-threaded sectors between them which is characterised as follows:

the height of the hexagonal projection is between 0.65 and 1.5 millimetres, the axial internally screw-threaded hole has a length from its exterior that does not exceed the lowest end of the straight upper cylindrical portion, with this length being between 3 and 5 millimetres, the height of the straight upper cylindrical portion is between 0.7 and 5 millimetres, the diameter of the screw-threaded cylindrical stem that starts from the above-mentioned cylindrical portion is between 2.5 and 6 millimetres, the conical end that finishes off the screw-threaded trunco-conical portion of the stern has an angle of approximately 120 degrees and is finished off by a flat chamfered surface of a generally circular shape, whose diameter is between 15 and 25% of the diameter of the screw-threaded portion of the stem, the longitudinal slots have, at the base of their cutting edges some portions which are outwardly curved concave rounded, from which there are other outwardly curved convex rounded portions that extend towards the cutting edges of the adjoining sector.

2. Dental implant, in accordance with claim 1, characterised in that when the implant has a diameter of more than 3 millimetres, the internal blind hole can exceed the lowest plane of the straight cylindrical portion.

* * * * *